US012575727B2

(12) United States Patent
Debrunner et al.

(10) Patent No.: US 12,575,727 B2
(45) Date of Patent: Mar. 17, 2026

(54) EYE TRACKING DEVICE, EYE TRACKING METHOD, AND COMPUTER-READABLE MEDIUM

(71) Applicant: INIVATION AG, Zürich (CH)

(72) Inventors: Thomas Debrunner, Zürich (CH);
Pierre Giraud, Opfikon (CH)

(73) Assignee: INIVATION AG, Zürich (CH)

( * ) Notice: Subject to any disclaimer, the term of this patent is extended or adjusted under 35 U.S.C. 154(b) by 0 days.

(21) Appl. No.: 18/574,471

(22) PCT Filed: Jun. 27, 2022

(86) PCT No.: PCT/EP2022/067614
§ 371 (c)(1),
(2) Date: Dec. 27, 2023

(87) PCT Pub. No.: WO2023/274981
PCT Pub. Date: Jan. 5, 2023

(65) Prior Publication Data
US 2024/0335110 A1      Oct. 10, 2024

(30) Foreign Application Priority Data
Jul. 2, 2021      (EP) ..................................... 21183557

(51) Int. Cl.
*A61B 3/113* (2006.01)
*A61B 3/15* (2006.01)
(Continued)

(52) U.S. Cl.
CPC .............. *A61B 3/113* (2013.01); *A61B 3/152* (2013.01); *G06F 3/013* (2013.01); *G06V 10/82* (2022.01); *G06V 40/19* (2022.01)

(58) Field of Classification Search
CPC ......... A61B 3/113; A61B 3/152; G06F 3/013; G06V 10/82; G06V 40/19; G06V 20/20; G06V 40/18; G06T 7/73
(Continued)

(56) References Cited

U.S. PATENT DOCUMENTS 10,417,784 B1 * 9/2019 Cavin .................... G06V 40/19
10,466,779 B1 11/2019 Liu
(Continued)

FOREIGN PATENT DOCUMENTS

EP      3 598 274 A1      1/2020
EP      3 933 550 A1      1/2022
(Continued)

*Primary Examiner* — Loi H Tran
(74) *Attorney, Agent, or Firm* — Christensen, Fonder, Dardi & Herbert PLLC; John P. Fonder

(57) ABSTRACT

An eye tracking device that includes: an event-based optical sensor configured to receive radiation reflected off an eye of a user and produce a signal stream of events, each event corresponding to detection of a temporal change in the received radiation at pixels of the sensor; glint sources configured to send radiation to the eye that is reflected off the cornea and received by the sensor in the form of individual glints; a controller connected to the sensor and configured to receive the signal stream from the sensor and to generate: gaze information of the eye and first glint information of the glints, at a first instant of time; and second glint information of the glints at a second instant of time that is later than the first instant of time. The controller is configured to generate predicted gaze information at the second instant of time.

18 Claims, 3 Drawing Sheets

(51) Int. Cl.
    *G06F 3/01*           (2006.01)
    *G06V 10/82*        (2022.01)
    *G06V 40/19*        (2022.01)

(58) Field of Classification Search
    USPC .......................................................... 348/78
    See application file for complete search history.

(56)                References Cited

U.S. PATENT DOCUMENTS

2020/0278539 A1 *   9/2020   Petljanski .............. G09G 3/003
2020/0372678 A1     11/2020   Farmer et al.

FOREIGN PATENT DOCUMENTS

| JP | 2020-536309 A | 12/2020 |
| WO | WO2019/067731 A1 | 4/2019 |
| WO | WO 2019/147677 A1 | 8/2019 |
| WO | WO2020/154524 A1 | 7/2020 |
| WO | WO2021/112990 A1 | 6/2021 |

* cited by examiner

EYE TRACKING DEVICE, EYE TRACKING METHOD, AND COMPUTER-READABLE MEDIUM

RELATED APPLICATIONS

The present application is a National Phase entry of PCT Application No. PCT/EP2022/067614, filed Jun. 27, 2022, which claims priority to European Patent Application No. 21183557.4, filed Jul. 2, 2021, the disclosures of which are hereby incorporated by reference herein in their entirety.

FIELD OF THE INVENTION

The invention relates to an eye tracking device, an eye tracking method, and a computer-readable medium.

BACKGROUND OF THE INVENTION

Eye tracking generally refers to the monitoring of the movement of the eye or the gaze of a human being, called a user. However, the user may of course also be any other living creature having an eye that can change its viewing direction in its socket.

One possible way of tracking a user's gaze is by way of a conventional video or photo camera that obtains full frames of images, or conventional frames, of the eye at intervals. A controller connected to the camera then analyses each of these image frames to determine the position of the pupil at the time the frame was captured, thus allowing it to deduce the direction the user is looking. This method necessitates the use of a frame-based camera, such as a video or photo camera, which obtains images of the eye for the controller to analyze. Such conventional or frame-based cameras are often slow. They also produce a large volume of data that needs to be transferred between the camera and the controller.

The eye tracking process can be accelerated by utilizing an event-based camera or event-based sensor, also called a dynamic vision sensor (DVS). EP 3598274 A1 describes a system comprising multiple cameras, where one of the cameras is an event-based camera or DVS. U.S. Ser. No. 10/466,779 A1 describes an eye tracking system that uses DVS data and outlines a method to convert the received DVS data into an intensity image, similar to a conventional frame.

A method which combines the acquisition of a purely event-based sensor output with a machine learning approach using convolutional neural networks for eye tracking is described in WO 2019147677 A1. Therein is described a system that accumulates events from an event camera to produce either intensity images, frequency images or time-stamp images, which are subsequently fed into a neural network algorithm to predict various gaze parameters. The described system uses a hand-crafted, static accumulation regime, a common and well-known technique to create an approximation of an intensity image from event data. An improved method combining the acquisition of a purely event-based sensor output with a machine learning approach using convolutional neural networks for eye tracking is described in the European patent application EP20184020.4. This improved method comprises receiving a signal stream of events generated by an event-based optical sensor due to radiation reflected off an eye of a user and received by the event-based optical sensor, generating by way of a first artificial neural network an inference frame to be utilized as input to a machine learning module, operating the machine learning module to obtain output data, and extracting from the output data the sought after information relating to the eye of said user. With this method, in particular a position or gaze direction of a pupil may be extracted, which may be called "pupil extraction" in the following. While this method leads to a more reliable tracking the eye movement, the extraction process takes time, leading to a relatively high latency.

SUMMARY

It is therefore an objective of the present invention to suggest a device and a method for more quickly tracking the movement of a user's eye.

This objective is met according to the present invention by providing an eye tracking device with the features of claim 1, an eye tracking method with the features of claim 12, and computer-readable medium with the features of claim 13. Further advantageous embodiments of the invention are subject of the sub-claims.

According to the invention, an event-based optical sensor and a controller connected to the sensor. Radiation reflected off an eye of a user is received by the event-based optical sensor, which is configured to produce a signal stream of events in response to the radiation. This signal stream is sent to the controller, which performs various processes on the signal stream in order to obtain the result of the eye tracking process. The controller may therefore comprise at least a processing unit and a memory for performing the analysis described in the following. In the following, the event-based optical sensor will just be called the event sensor.

The sensor, in particular a dynamic vision sensor, comprises a number of individual pixels arranged in an array, each pixel having a photosensitive cell or a photosensitive area. Upon detection of a temporal change in the incident light impinging on that photosensitive cell, an event signal, herein just called "an event", is generated. Each event in the signal stream of events produced by the sensor thus corresponds to the detection of a temporal change in the received radiation at one or more pixels of said optical sensor. Each event may in particular comprise the position of the corresponding pixel in the array, an indicator showing the polarity and optionally also the magnitude of the temporal change, and the time the change occurred. The events or event data are/is sent as part of the signal stream to the controller for further processing.

The eye tracking device further comprises one or more glint sources. The glint sources are radiation sources that are configured to send radiation to the eye of the user such that said radiation is reflected off the cornea of said eye and is received by said event sensor in form of one or more individual glints. Typically, there are between 8 and 15 glint sources, leading to between 4 and 8 glints on the eye, preferably on the cornea of the eye, at any given time.

As both the reflected light from the glint sources and other radiation reflecting off the surface of the eye strikes the event sensor, the signal stream received by the controller can be utilized to obtain information on the eye as a whole as well as information on the position of the glints on the surface of the eye or the sensor plane. The controller is configured to extract this gaze information and this glint information. The invention is based on the concept of utilizing the glint information to predict gaze information whenever newly extracted gaze information is not available. In other words, the glint information will be utilized to predict information on the gaze in-between instances when actual gaze information is extracted by the controller. Because extracting glint information from the signal stream of events and predicting gaze information from the glint information takes less time than extracting gaze information from the signal stream of events, it is thus possible to update the gaze information with the help of the predicted gaze information at higher frequency and therefore reduce latency.

The controller is thus configured to generate gaze information and first glint information. The generated gaze information and first glint information of said one or multiple glints are from a first instant of time. They are thus synchronous or substantially synchronous. That means that they describe the status of the gaze and the status of the glints, in particular the position of the glints, at the first instant of time. The first instant of time may in particular be the instant when the radiation coming from the eye and containing the gaze and glint information arrives at the event sensor. The controller is further configured to generate second glint information of said one or multiple glints at a second instant of time that is later than the first instant of time. Utilizing the second glint information, the controller generates predicted gaze information of the eye. The predicted gaze information here is information that is not extracted directly from the received signal stream as is the gaze information at the first instant of time. The latter may at some points be called "extracted" gaze information to avoid confusion.

According to an advantageous embodiment, the controller is configured to generate said predicted gaze information based on said second glint information, said gaze information, and said first glint information. The gaze information and the first glint information may be utilized to find a relationship between glint information and gaze information, such that consecutively determined second glint information can be utilized for predicting gaze information at the second instant of time.

The controller is preferably configured to determine model parameters based on said gaze information and on said first glint information, and to generate said predicted gaze information based on said second glint information and said model parameters. In particular, the model parameters may be obtained by vector and/or matrix manipulation techniques, wherein the gaze information is arranged in a gaze matrix and the first glint information is arranged in a glint information matrix, while the model parameters are determined in a vector. A predicted gaze information matrix may then be calculated using the second glint information arranged in a second glint information matrix and the model parameters. In a further step, the predicted gaze information may be taken from the predicted gaze information matrix.

According to a preferred embodiment, the controller is configured to repeatedly generate gaze information and corresponding first glint information and to update said model parameters based on multiple previously generated gaze information and corresponding first glint information. Previously in this case means in particular that the gaze information and corresponding first glint information on which the model parameters are based have are from before the time of updating the model parameter. In other words, as mentioned before, the controller generates the gaze information and the first glint information at a first instant of time. Then, the controller generates further gaze information and further first glint information at a second instant of time, which is later than the first instant of time. As with the first instant of time, that the further gaze information and further first glint information are from the second instant of time may in particular mean that the radiation coming from the eye and containing the further gaze and glint information arrives at the event sensor at that second instant of time. Between generating the gaze and first glint information on the one hand and generating further gaze and first glint information on the other hand, the controller will generate at least one, however preferably two or multiple, predicted gaze information.

As a clarification, first glint information in particular refer to glint information that is extracted simultaneously with gaze information. Both the extracted gaze information and the extracted first glint information form part of the input data for training the model, as described further below. This applies also to any further first glint information, which is also paired with corresponding gaze information and added to the training data for training o updating the model. On the other hand, the second glint information is in particular glint information that is not added to and used as training data to train or update the model. This may for example be because there exists for the second glint information no (temporally) corresponding gaze information. The second glint information is advantageously only used to predict gaze information with the help of the model.

Advantageously, the controller is configured to repeatedly generate gaze information and to repeatedly generate predicted gaze information, wherein said predicted gaze information are generated at a rate of at least 2 times, 3 times, 5 times or 8 times the rate at which said gaze information are generated. For example, gaze information may be generated every 2 milliseconds (ms), while predicted gaze information may be generated every 0.5 ms. This would mean that between every two gaze information generations three predictions of gaze information will take place. Thus, in this case, the predicted gaze information is generated at a rate of three times that of the generation of the extracted gaze information.

If multiple glint sources are utilized, they may advantageously be arranged to produce multiple glints at different positions, in particular at different positions on the surface of the eye and/or at different positions in the sensor plane of the optical sensor. Advantageously, a number of between 5 and 20 glint sources may be utilized, preferably between 8 and 18 glint sources, more advantageously between 10 and 15 glint sources. The number of glints visible by the optical sensor at any given time is usually much lower than the number of glint sources utilized. As an example, when the eye tracking device comprises 12 glint sources, usually around 6 glints will be detectable by the device at any given time.

Preferably, said one or multiple glint source(s) is/are configured to send temporally modulated radiation to the eye. By locking onto the utilized modulation frequency at which the radiation is modulated, the controller may better distinguish between the radiation from the glint source(s) and other radiation reflecting off the eye or otherwise reaching the optical sensor, thus allowing for improved glint extraction. The modulation frequency may advantageously lie between 0.2 kHz and 5 kHz, more advantageously between 0.5 kHz and 2 kHz.

The eye tracking device preferably comprises at least two glint sources, which are configured to send temporally modulated radiation to said eye, wherein radiation from one of said glint sources has a different modulation frequency than radiation from the other of said glint sources. When utilizing three or more glint sources, the modulation frequencies of the glint sources may be mutually different. Alternatively, within glint sources with mutually different modulation frequencies, there may be one or more groups glint sources, wherein the glint sources in a group have essentially the same modulation frequency. The modulation frequency or any one of the modulation frequencies described above may be either known or unknown to the controller.

Preferably, the controller is configured to generate said gaze information based solely on the signal stream of events, without having to access image frames collected by a conventional frame-based camera. Advantageously, said controller is configured to generate said gaze information utilizing a machine learning module. In particular, the controller is configured to generate said gaze information utilizing an artificial neural network, for example a recurrent neural network, preferably a recurrent neural network having at least one memoized layer. The controller may utilize an artificial neural network for generating an inference frame and then handing the generated inference frame to a machine learning module. In this embodiment, the artificial neural network is used to transform the stream of events into an inference frame, which can then be handled by the machine learning module. Alternatively, the controller may be configured to use a hand-crafted, static accumulation regime to create an inference frame from the event data to input into the machine learning module. The use of such artificial neural networks is described in detail in EP20184020.4, which is included herein by reference in its entirety.

A recurrent neural network, in short RNN, means in particular that the last output from the RNN is fed back to or fed into the RNN in some way, e.g. at the last layer, at the first layer and/or at some layer in-between. Advantageously, the output of the RNN is fed back to the input of the RNN. In particular, the output of the RNN after one execution of the RNN algorithm may be utilized as one of multiple inputs to the RNN during a consecutive execution of the RNN algorithm.

The artificial neural network may comprise multiple layers, one, two or more of which may be convolutional layers. In case the artificial neural network is an RNN, it may thus also be called a convolutional recurrent neural network. The artificial neural network may also comprise a concatenation layer, in particular as a first layer, in order to join, or concatenate, the output after an execution and the new input for a consecutive execution of the neural network algorithm. Furthermore, the neural network may comprise one, two or more non-linear activation functions, in particular a rectifier, and/or a normalization layer.

Preferably, one, two or more of the layers of the artificial neural network is/are memoized layer(s). A memoized layer stores the results of that layer during the latest pass, i.e. during the latest execution of the neural network algorithm. The memoized layer allows for an implementation, wherein during every pass only the stored values of the memoized layer are updated that depend on a tensor element that is non-zero in the input sparse tensor. This technique significantly accelerates the neural network inference speed and, in some embodiments, can lead to better quality inference frames for the consecutive machine learning module.

The idea behind utilizing one or multiple memoized layers is that when only very little changes in the previous layer, it is sufficient to only update the internal values/states of the neural network that are affected. This can save processing power on updating the states in the neural network. Besides convolutional layers, also non-linear activation functions and/or normalization layers may be memoized. Advantageously, every convolutional layer and/or every non-linear activation function may be of a memoized kind. In this case, in every layer, only the values are updated that are directly affected by a change in the input.

In accordance with a preferred embodiment, the machine learning module comprises a further artificial neural network.

According to an advantageous embodiment, said controller is configured to generate said first glint information and/or said second glint information with the help of a frequency-based algorithm. In particular, such a frequency-based algorithm may be implemented by filtering the input using a discrete Fourier transformation (DFT).

The herein described gaze information may comprise a gaze direction of said user, a pupil center position of said eye of said user, a pupil outline of said eye of said user, and/or an eye lid position of said eye of said user. These are important attributes that may be of interest for the eye-tracking device to acquire. Consequently, the controller is advantageously configured to generate one or multiple of these attributes based on said signal stream of events.

The event sensor of the eye tracking device may be provided with optical filters in order for it to only detect radiation from a certain range of wavelengths, such as infrared (IR) radiation, in particular an infrared band-pass filter. While it is possible that the radiation reflecting off the eye is ambient light, such an approach has the disadvantage that it might produce parasitic signals due to possibly low radiation levels or light disturbances. Therefore, advantageously, a radiation source is provided, which is configured to send radiation to the eye of the user such that it is reflected off that eye and is received by the event-based optical sensor. In order for the radiation source to not disturb the user, the radiation it produces should be well outside of the visible regime. Preferably, the radiation source is an infrared (IR) emitter.

Said radiation source is further configured such that the radiation sent to the eye is substantially continuous wave and/or that the radiation sent to the eye illuminates substantially the entire cornea or the entire exposed surface of said eye. These additional features may be used by the controller to distinguish the radiation coming from the radiation source from the radiation coming from the glint source.

The radiation source and/or the glint source(s) may preferably be made of solid-state components, in particular light emitting diodes (LEDs), and/or comprise organic material, such as an organic light emitting diode (OLED).

Advantageously, the eye tracking device comprises a body mountable apparatus, in particular a head-mountable apparatus, for mounting the eye tracking device to the body of said user, in particular to his or her head. The fields of application for such a device may include virtual reality or augmented reality, where it can support the implementation of foveated rendering.

Preferably, the gaze information and/or the predicted gaze information generated by the controller is sent to computing device. The computing device may utilize the received information as an input or as one of multiple inputs for controlling or manipulating a program, algorithm and/or process run on the computing device. The information may be stored and/or processed by the controller before being sent to the computing device. As an example, the computing device may be running a virtual reality program, controlling a screen in a headset of a user. The images and video shown in the screen may then be dependent on the gaze information and the predicted gaze information provided by the controller.

According to a further aspect of the invention, an eye tracking method and a computer-readable medium are provided. Any features described above in connection with the eye tracking device may also be used alone or in suitable combinations in the eye tracking method or the computer-readable medium.

BRIEF DESCRIPTION OF THE DRAWINGS

Some examples of embodiments of the present invention will be explained in more detail in the following description with reference to the accompanying schematic drawings, wherein.

DETAILED DESCRIPTION

Figure 1:
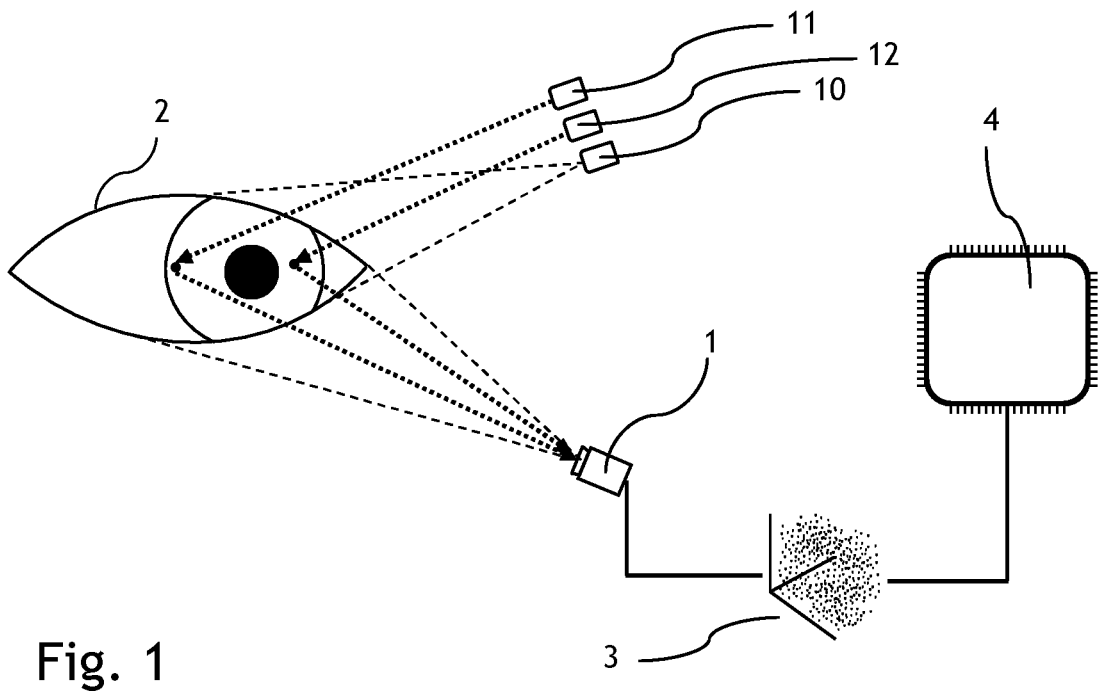
FIG. 1 shows a schematic diagram of the setup of an eye-tracking device according to one preferred embodiment.

FIG. 1 shows in a schematic diagram the setup of an eye-tracking device according to a preferred embodiment. A radiation source 10 sends out radiation (represented by dashed lines) that is reflected off an eye 2 of a user, which is to be tracked. The reflected radiation (represented by dashed lines) is incident on an event-based optical sensor 1, or event sensor 1 in short. The radiation source 10, the event sensor 1, and an optical lens (not shown) for focusing the radiation are mounted onto a head-mountable device (not shown), such as glasses, virtual reality (VR) or augmented reality (AR) devices. The event sensor 1 is equipped with an infrared band-pass filter. Eye movements cause changes in the light intensity of the radiation 12 reflected off the user's eye 2. These light intensity changes or variations are picked up by the event sensor 1. In response, the event sensor 1 generates a stream 3 of light change events, which are transmitted to a controller 4 for processing.

This processing may include a preprocessing of the stream 3 of events to obtain suitable input for a recurrent neural network (RNN), performing the RNN on the preprocessed data to obtain an inference frame and performing a convolutional neural network (CNN) for estimating desired attributes. However, further additional and/or alternative processing steps can be utilized in order for the controller to obtain gaze information. It should be also noted that instead of the radiation source 10, ambient light may be utilized as radiation that is reflected off the eye and detected by the event sensor 1.

Also shown in FIG. 1 are two glint sources 11, 12. This may only be for clarity reasons, as usually a larger number of glint sources may be advantageous, such as 10, 12 or 14 glint sources. Each glint source 11, 12 sends out radiation towards the eye 2, which is shown in FIG. 1 in the form of arrows leading form the glint sources 11, 12 to the eye 2. The reflected light, shown as arrows leaving the eye, impinges on the event sensor 1. The radiation from the glint sources 11, 12 is received by the event-based optical sensor in form of glints. If in fact only two glint sources 11, 12 were utilized, the number of glints visible on the event sensor 1 plane as coming from the cornea 21 of the eye 2 could be zero, one or two at any given instant of time, depending on the orientation of the eye 2, the glint sources 11, 12 and the event sensor 1 with respect to each other.

Because both the radiation originating from the radiation source 10 and the radiation originating from the glint sources 11, 12 impinges on the event sensor, the stream 3 of events produced by the event sensor 1 will also be dependent on both. It is the controller's 4 responsibility to extract both gaze information and gaze information from the stream 3 of events received from the event sensor 1.

Figure 2:
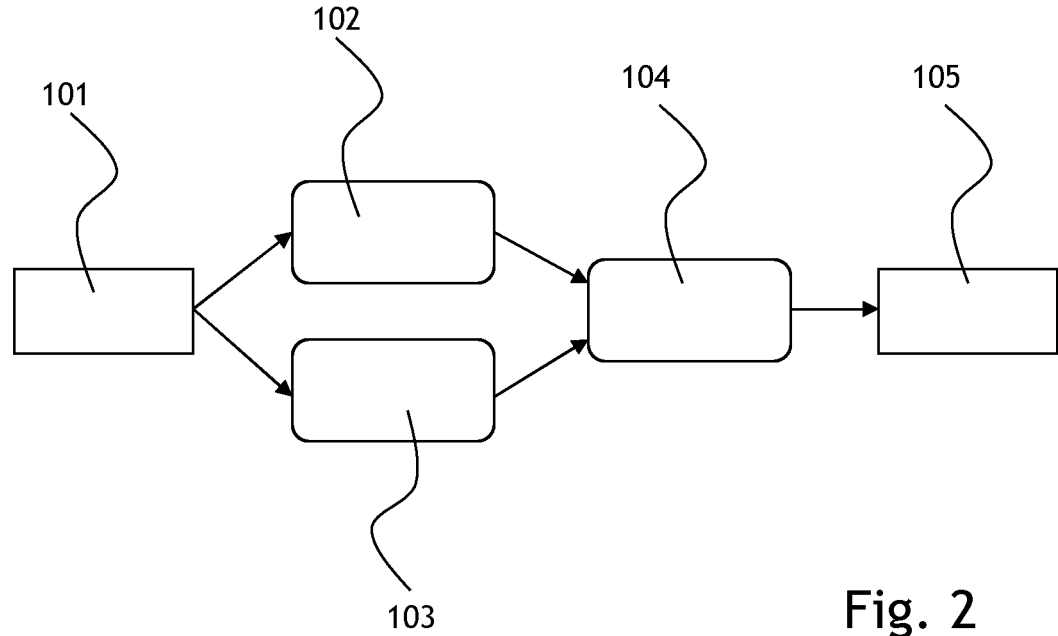
FIG. 2 shows a flow chart visualizing the coarse structure of the process of predicting gaze information.

The flow chart in FIG. 2 visualizes the coarse structure of the process of predicting gaze information according to a preferred embodiment. In a first step 101, the controller receives the event data generated by the event sensor 1 in form of a signal stream 3 of events. The controller 4 extracts (step 103) gaze information from the event data, such as a pupil position. As mentioned before, the extraction of the gaze information may be performed utilizing an extraction module that comprises a machine learning module and/or an artificial neural network. The controller 4 further extracts (step 102) glint information from the event data, in particular the position of one or multiple glints on the cornea 21 of the eye 2. In a following step 104, the extracted gaze information and glint information are utilized to calculated model parameters. These model parameters can then be utilized to predict 105 gaze information, i.e. to generate predicted gaze information, for time instances for which extracted gaze information is not available.

One possible model that can be utilized in connection with the herein described eye tracking device will be discussed in the following. This model is designed to predict pupil information based on glint positions. Its concept is based on live training. The "training" data for the model is a set of N pairs $\{P_t, \{G_1, G_2, \ldots, G_n\}_t\}$. Each pair contains pupil data $P_t$ at timestamp t, and glint data $G_1, G_2, \ldots, G_n$ regarding n glint(s) at timestamp t. The pupil data may in particular describe the position and/or orientation of the pupil, while the glint data may describe the position of the glint(s), with $G_n$ being the glint data for an n-th glint.

After accumulation of a suitable number of pairs of glint data/pupil data, where the glint data and pupil data in each pair are aligned in time, a model can be initialized with specific parameters (for example number of glints and/or power) depending on the number of pairs that have been retrieved. The model is designed to continuously adapt to the number and combination of detected glints. In other words, the model can be updated and predict on any encountered glint combination.

Given a set of n Glints $G=\{G_1, G_2, \ldots, G_n\}$, by using their horizontal x coordinates and their vertical y coordinates, a data matrix V can be defined, composed of the value 1 and the alternating x and y coordinates of each glint at every timestamp t. Thus, one row of V may be defined as the following: $[1, x_{G1}, y_{G1}, x_{G2}, y_{G2}, \ldots, x_{Gn}, y_{Gn}]$. Similarly, a data matrix P may be constructed for the known, i.e. extracted, pupil data composed at each row of the pupil center coordinates, x and y at a given timestamp t.

From the glint data matrix V, a model matrix M may be constructed, where each row is defined based on a row of V at a specified timestamp t. Each row of the model matrix M may for example be defined as the enumeration of all product combinations of p elements of this row of V (where p is the power in the model previously defined). An example of a row of the model matrix M is given next with n=2 glints, power p=2 as:

$$[1 \ x_{G1} \ x_{G1} \cdot x_{G1} \ x_{G1} \cdot y_{G1} \ x_{G1} \cdot x_{G2} \ x_{G1} \cdot y_{G2} \ y_{G1} \ y_{G1} \cdot y_{G1}$$
$$y_{G1} \cdot x_{G2} \ y_{G1} \cdot y_{G2} \ x_{G2} \ x_{G2} \cdot x_{G2} \ x_{G2} \cdot y_{G2} \ y_{G2} \ y_{G2} \cdot y_{G2}]$$

The model finally uses the matrix equation P=M*β, which will be solved to produce a model parameter β, a vector, which is later used to predict gaze information based only on extracted glint information.

The first calculation of the model parameter β as described above may be regarded as an initialization step of the model. Once initialized, the model can be updated by adding all new pairs of pupil data and glint data {$P_t$, $G_t$} to the existing "training" data. In the updated mode, the model parameter β is then redefined with the help of the data matrix P and the model matrix M, which are now created based on new set of data.

As soon as the model is defined by obtaining the model parameter β, i.e. initiated, as well as after every update, the model can be used on any set of glint data at a given timestamp t to predict a corresponding pupil data $P_t$.

For the prediction stage, $M_t$ may be defined using the above steps of preparing a glint data matrix $V_t$ and constructing the model matrix $M_t$ from the latest or newest set of glints. Similarly, β is the latest model parameter obtained. From these, the predicted pupil data can be calculated with the equation $P_t$=$M_t$*β.

While the above paragraphs mention pupil data, $P_t$ may in fact refer to a parameterization of any useful gaze information, such as gaze direction, pupil center position, pupil outline, eye lid position etc. Likewise, $G_n$ refers to a parameterization of glint information for one glint, such as the location of a glint on the pupil or cornea. The collection of glint information of all extracted glints at a given time t, i.e. with a given timestamp t, is defined as $G_t$.

Figure 3:
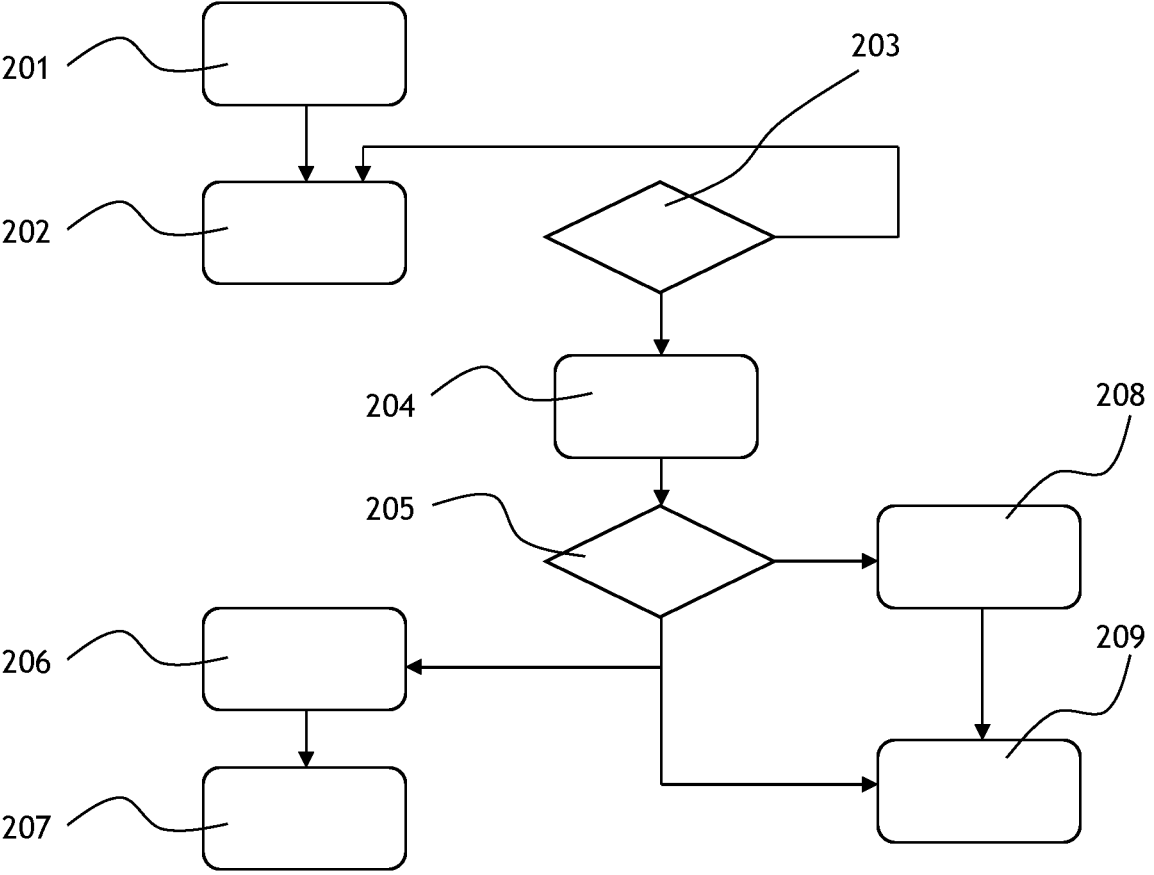
FIG. 3 shows a flow chart of different processing steps performed by an eye tracking device according to a preferred embodiment.

The steps performed by the eye tracking device to implement the above described or a similar model is visualized in FIG. 3. In an initialization step 201, the model is initialized, in particular by allocating parameter memory for the various parameters and variables of the model. Initialization of the model may also include the generation of an empty model that predicts a default gaze information, such as a default pupil position. In a following step 202, input data for the model is acquired by extracting from the signal stream 3 of events gaze information and/or glint information, if such glints can be detected. It is then determined 203, whether at least one glint could be extracted. If this is not the case, the process returns back to the step of acquiring input data 202. In the case that at least one glint could be extracted, in a further step 204, the number of extracted glints and the size of the "training" data is used as a basis to obtain a model degree p. As the signal stream 3 is continuously monitored by the controller 4, new gaze information and/or glint information may continuously be extracted. If any such new data becomes available 205, then this new data will be stored 206 as training data for training and updating 207 the model.

Finally, the gaze information obtained by the process may be outputted 209 as current or the latest gaze information. This outputted gaze information may either be extracted gaze information that has been obtained directly from the signal stream 3, or it may be predicted gaze information predicted by the model used in the eye tracking method.

Figure 4:
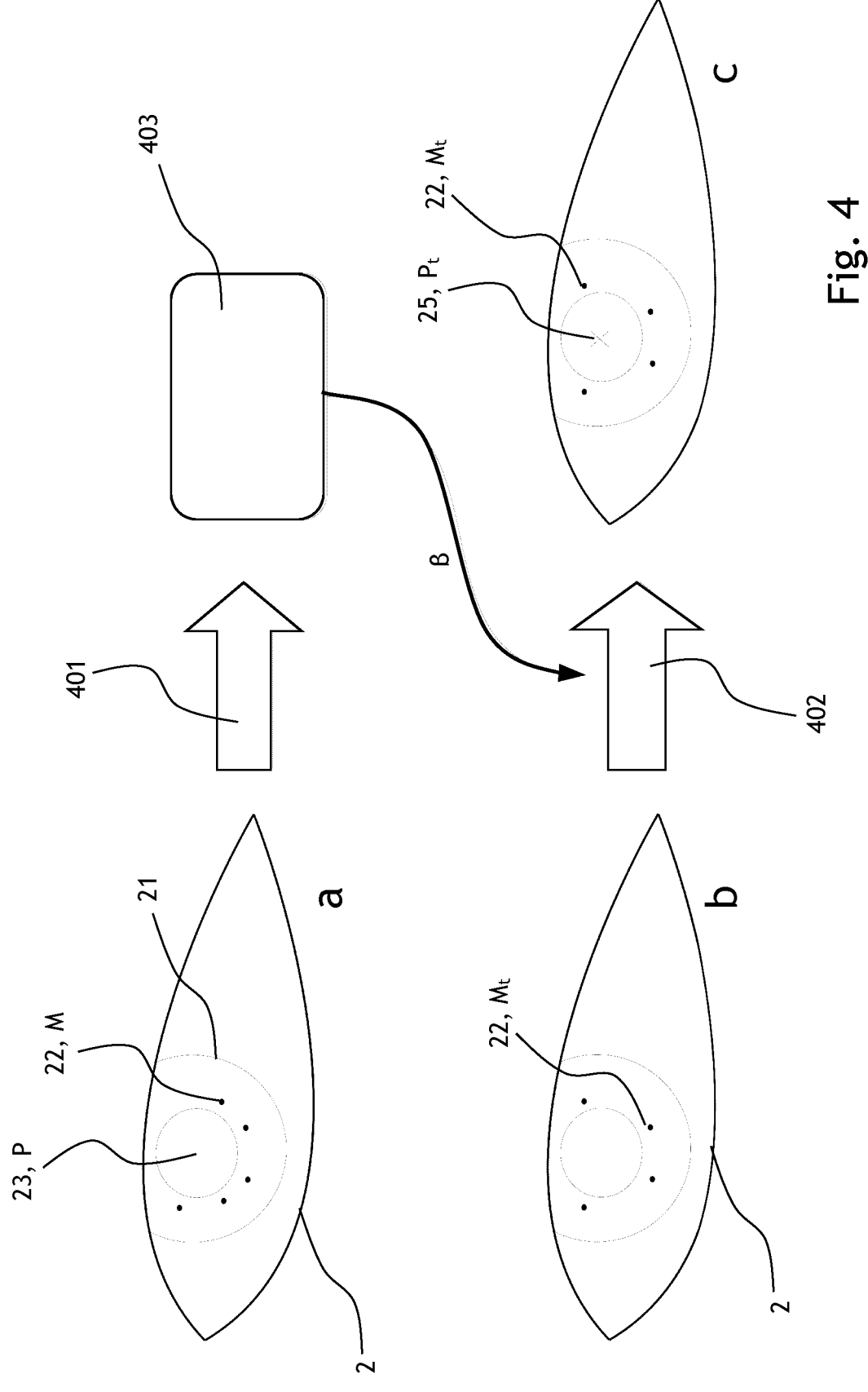
FIG. 4 shows a schematic visualizing the steps in a process by an eye tracking device according to a preferred embodiment.

The process described above is visualized in a more intuitive manner in FIG. 4. Inside the eye 2, the pupil center position 23, which is one possible gaze information, is indicated together with glints 22 distributed around the pupil on the cornea 21 of the eye 2. In the eye schematic labelled "a", The pupil center position 23 is the actual position of the pupil center, corresponding to an extracted gaze information that is extracted directly from the signal stream 3 provided by the event sensor 1. Furthermore, five glints 22 are shown in the schematic labelled "a", which are indicative of the glint information extracted from the signal stream 3. Because the extraction of the gaze information and glint information coincide, the gaze information and glint information corresponding to the pupil center position 23 (indicated by a "+") and the five glints 22 (indicated by dots) form a pair of data that is either used to initialize the model or that is added to existing data and used to update 401 the model 403.

In a later step, visualized by the eye schematic labelled "b", only glint information is extracted from the signal stream 3. In this specific example, the glint information corresponds to only four glints 22 on the cornea. Not gaze information is extracted in this step, as visualized by the missing "+". Utilizing the initiated or updated model 403 (as indicated by the thin solid arrow), the extracted glint information is used to calculate or predict 402 a predicted gaze information in form of a predicted pupil center position 25 (indicated by a "x"), as visualized in the schematic labelled "c".

REFERENCE NUMERALS 1 event-based optical sensor, event sensor, DVS sensor
10 radiation source, IR emitter
11, 12 glint sources
2 eye of a user
21 cornea
22 glint
23 gaze information, pupil center position
25 predicted gaze information, predicted pupil center position
3 signal stream of events
4 controller
P extracted gaze information
M first glint information
$P_t$ predicted gaze information
$M_t$ second glint information

The invention claimed is:

1. An eye tracking device comprising:

an event-based optical sensor which is configured to receive radiation reflected off an eye of a user and to produce a signal stream of events, each event corresponding to detection of a temporal change in the received radiation at one or more pixels of said optical sensor;

one or more glint sources configured to send radiation to the eye of the user such that said radiation is reflected off the cornea of said eye and is received by said event-based optical sensor in a form of one or more individual glints;

a controller which is connected to said optical sensor and configured to receive the signal stream of events from said optical sensor and to generate based on said signal stream of events:

gaze information of said eye at a first instant of time;

first glint information of said one or multiple glints at said first instant of time; and second glint information of said one or multiple glints at a second instant of time that is later than the first instant of time, and wherein said controller is configured to extract said gaze information from the signal stream of events utilizing an extraction module that comprises a machine learning module and/or an artificial neural network, and to generate predicted gaze information of said eye at said second instant of time based on said second glint information and model parameters, which are live-trained using glint data and pupil data prior to the next extraction of gaze information.

2. The eye tracking device according to claim 1, wherein said controller is configured to generate said predicted gaze information based on said second glint information, said gaze information, and said first glint information.

3. The eye tracking device according to claim 1, wherein said controller is configured to determine model parameters based on said gaze information and on said first glint information.

4. The eye tracking device according to claim 3, wherein said controller is configured to repeatedly generate gaze information and corresponding first glint information and to update said model parameters based on multiple previously generated gaze information and corresponding first glint information.

5. The eye tracking device according to claim 1, wherein said controller is configured to repeatedly generate gaze information and to repeatedly generate predicted gaze information, wherein said predicted gaze information are generated at a rate of at least 2 times the rate at which said gaze information is generated.

6. The eye tracking device according to claim 1, wherein said one or multiple glint source(s) is/are configured to send temporally modulated radiation to the eye.

7. The eye tracking device according to claim 6, wherein at least two glint sources are configured to send temporally modulated radiation to said eye, wherein radiation from one of said glint sources has a different frequency than radiation from the other of said glint sources.

8. The eye tracking device according to claim 1, wherein said controller is configured to generate said gaze information utilizing an artificial neural network, in particular a recurrent neural network, preferably a recurrent neural network having at least one memoized layer.

9. The eye tracking device according to claim 1, wherein said controller is configured to generate said first glint information and/or said second glint information with the help of a frequency based algorithm.

10. The eye tracking device according to claim 1, wherein said gaze information comprises a gaze direction of said user, a pupil center position of said eye of said user, a pupil outline of said eye of said user, and/or an eye lid position of said eye of said user.

11. The eye tracking device according to claim 1, further including a radiation source configured to send radiation to the eye of the user such that it is reflected off said eye of the user and is received by said event-based optical sensor, wherein said radiation source is configured such that the radiation sent to the eye is substantially continuous wave and/or that the radiation sent to the eye illuminates substantially the entire cornea or the entire exposed surface of said eye.

12. The eye tracking device according to claim 5, wherein said controller is configured to repeatedly generate gaze information and to repeatedly generate predicted gaze information, wherein said predicted gaze information are generated at a rate of at least 3 times the rate at which said gaze information is generated.

13. The eye tracking device according to claim 5, wherein said controller is configured to repeatedly generate gaze information and to repeatedly generate predicted gaze information, wherein said predicted gaze information are generated at a rate of at least 5 times the rate at which said gaze information is generated.

14. The eye tracking device according to claim 5, wherein said controller is configured to repeatedly generate gaze information and to repeatedly generate predicted gaze information, wherein said predicted gaze information are generated at a rate of at least 8 times the rate at which said gaze information is generated.

15. The eye tracking device according to claim 8, wherein said artificial neural network is a recurrent artificial neural network.

16. The eye tracking device according to claim 15, wherein said recurrent artificial neural network has at least one memoized layer.

17. An eye tracking method, comprising the following steps:

sending radiation to the eye of a user by one or more glint sources such that said radiation is reflected off the cornea of said eye and is received by said event-based optical sensor in a form of one or more individual glints;

receiving a signal stream of events produced by an event-based optical sensor due to radiation reflected off the eye of the user being received by said event-based optical sensor, each event corresponding to detection of a temporal change in the received radiation at one or more pixels of said optical sensor; and generating based on said signal stream of events:

gaze information of said eye at a first instant of time, extracted by an extraction module that comprises a machine learning module and/or an artificial neural network, first glint information of said one or multiple glints at said first instant of time, and second glint information of said one or multiple glints at a second instant of time that is later than the first instant of time, wherein said predicted gaze information of said eye is generated at said second instant of time based on said second glint information; and model parameters, which are live-trained using glint data and pupil data prior to the next extraction of gaze information.

18. A computer-readable medium comprising instructions which, when executed by a computer or microcontroller, cause the computer or microcontroller to carry out the following steps:

sending radiation to the eye of a user by one or more glint sources such that said radiation is reflected off the cornea of said eye and is received by said event-based optical sensor in form of one or more individual glints;

receiving a signal stream of events produced by an event-based optical sensor due to radiation reflected off the eye of the user being received by said event-based optical sensor, each event corresponding to detection of a temporal change in the received radiation at one or more pixels of said optical sensor; and generating based on said signal stream of events:

gaze information of said eye at a first instant of time, extracted by an extraction module that comprises a machine learning module and/or an artificial neural network, first glint information of said one or multiple glints at said first instant of time, and second glint information of said one or multiple glints at a second instant of time that is later than the first instant of time, wherein said predicted gaze information of said eye is generated at said second instant of time based on said second glint information and model parameters, which are live-trained using glint data and pupil data prior to the next extraction of gaze information.

\* \* \* \* \*